US009541834B2

(12) United States Patent
Pohlers et al.

(10) Patent No.: US 9,541,834 B2
(45) Date of Patent: Jan. 10, 2017

(54) IONIC THERMAL ACID GENERATORS FOR LOW TEMPERATURE APPLICATIONS

(71) Applicant: Rohm and Haas Electronic Materials LLC, Marlborough, MA (US)

(72) Inventors: Gerhard Pohlers, Needham, MA (US); Cong Liu, Shrewsbury, MA (US); Cheng-Bai Xu, Southborough, MA (US); Kevin Rowell, Brighton, MA (US); Irvinder Kaur, Westborough, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 276 days.

(21) Appl. No.: 13/691,689

(22) Filed: Nov. 30, 2012

(65) Prior Publication Data
US 2015/0212414 A1    Jul. 30, 2015

(51) Int. Cl.
| | | |
|---|---|---|
| *G03F 7/40* | (2006.01) | |
| *G03F 7/30* | (2006.01) | |
| *G03F 7/09* | (2006.01) | |
| *G03F 7/11* | (2006.01) | |
| *G03F 7/039* | (2006.01) | |
| *C07D 239/26* | (2006.01) | |
| *C07D 241/12* | (2006.01) | |
| *C07D 263/32* | (2006.01) | |
| *C07D 277/22* | (2006.01) | |
| *C07C 309/03* | (2006.01) | |
| *C07C 309/06* | (2006.01) | |
| *C07D 333/48* | (2006.01) | |

(52) U.S. Cl.
CPC ............. *G03F 7/40* (2013.01); *C07C 309/03* (2013.01); *C07C 309/06* (2013.01); *C07D 239/26* (2013.01); *C07D 241/12* (2013.01); *C07D 263/32* (2013.01); *C07D 277/22* (2013.01); *C07D 333/48* (2013.01); *G03F 7/0397* (2013.01); *G03F 7/09* (2013.01); *G03F 7/091* (2013.01); *G03F 7/11* (2013.01); *G03F 7/30* (2013.01); *G03F 7/405* (2013.01)

(58) Field of Classification Search
None
See application file for complete search history.

(56) References Cited

U.S. PATENT DOCUMENTS

| | | | |
|---|---|---|---|
| 3,474,054 | A | 10/1969 | White |
| 4,200,729 | A | 4/1980 | Calbo |
| 4,251,665 | A | 2/1981 | Calbo |

(Continued)

FOREIGN PATENT DOCUMENTS

| | | | |
|---|---|---|---|
| CN | 102117022 | * | 7/2011 |
| EP | 0164248 B1 | | 10/1991 |

(Continued)

OTHER PUBLICATIONS

Chemical Abstract for CN 102117022 (Accession No. 2011:857786) (2011).*

*Primary Examiner* — Sin Lee
(74) *Attorney, Agent, or Firm* — Mintz Levin Cohn Ferris Glovsky and Popeo, P.C.; Peter F. Corless

(57) ABSTRACT

New ionic thermal acid generator compounds are provided. Also provided are photoresist compositions, antireflective coating compositions, and chemical trim overcoat compositions, and methods of using the compositions.

16 Claims, 1 Drawing Sheet

(56) References Cited

U.S. PATENT DOCUMENTS

| | | | |
|---|---|---|---|
| 4,362,809 | A | 12/1982 | Chen et al. |
| 4,370,405 | A | 1/1983 | O'Toole et al. |
| 4,910,122 | A | 3/1990 | Arnold et al. |
| 5,100,768 | A * | 3/1992 | Niki et al. .................. 430/281.1 |
| 5,128,232 | A | 7/1992 | Thackeray et al. |
| 5,187,019 | A | 2/1993 | Calbo et al. |
| 5,304,456 | A * | 4/1994 | Ueda et al. ................ 430/270.1 |
| 5,492,793 | A | 2/1996 | Breyta et al. |
| 5,843,624 | A | 12/1998 | Houlihan et al. |
| 5,851,730 | A | 12/1998 | Thackeray et al. |
| 5,851,738 | A | 12/1998 | Thackeray et al. |
| 5,886,102 | A | 3/1999 | Sinta et al. |
| 5,939,236 | A | 8/1999 | Pavelchek et al. |
| 6,042,997 | A | 3/2000 | Barclay et al. |
| 6,057,083 | A | 5/2000 | Taylor et al. |
| 6,852,421 | B2 | 2/2005 | Wayton et al. |
| 7,968,268 | B2 | 6/2011 | Wang |
| 8,021,826 | B2 * | 9/2011 | Kim ..................... C09D 131/02 430/271.1 |
| 8,067,148 | B2 | 11/2011 | Endou et al. |
| 2009/0146322 | A1 | 6/2009 | Weling et al. |
| 2009/0297784 | A1* | 12/2009 | Xu et al. ....................... 428/172 |
| 2011/0274853 | A1* | 11/2011 | Park et al. .................... 427/595 |

FOREIGN PATENT DOCUMENTS

| | | | |
|---|---|---|---|
| EP | 0232972 | B1 | 9/1993 |
| WO | 9003598 | A1 | 4/1990 |

* cited by examiner

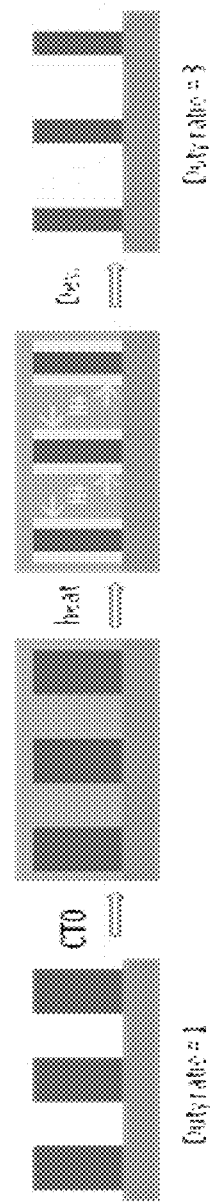

IONIC THERMAL ACID GENERATORS FOR LOW TEMPERATURE APPLICATIONS

FIELD

In one aspect, the present invention relates to new thermal acid generators having a low onset temperature, and to compositions comprising the thermal acid generators.

INTRODUCTION

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating.

Positive-tone chemically amplified photoresists are conventionally used for high-resolution processing. Such resists typically employ a resin having acid-labile leaving groups and a photoacid generator. Exposure to actinic radiation causes the acid generator to form an acid which, during post-exposure baking, causes cleavage of the acid-labile groups in the resin. This creates a difference in solubility characteristics between exposed and unexposed regions of the resist in an aqueous alkaline developer solution. Exposed regions of the resist are soluble in the aqueous alkaline developer and are removed from the substrate surface, whereas unexposed regions, which are insoluble in the developer, remain after development to form a positive image.

One approach to achieving nm-scale feature sizes in semiconductor devices is the use of short wavelengths of light, for example, 193 nm or less, during exposure of chemically amplified photoresists. To further improve lithographic performance, immersion lithography tools have been developed to effectively increase the numerical aperture (NA) of the lens of the imaging device, for example, a scanner having a KrF or ArF light source. It is possible to achieve a 40 nm half-pitch resolution in a single exposure process, thus allowing for improved design shrink. This standard immersion lithography process, however, is generally not suitable for manufacture of devices requiring greater resolution, for example, for the 32 nm and 22 nm half-pitch nodes.

To extend the practical resolution beyond that achieved with standard photolithographic techniques, chemical trimming processes have been proposed for reducing the critical dimension (CD) of a photoresist pattern. Chemical trimming processes typically involve treating a photoresist pattern with a composition including an acid or acid generator capable of increasing solubility of a surface region of the photoresist pattern in a developer solution. Such a process is disclosed, for example, in U.S. Pat. No. 8,067,148, which discloses a chemical trimming solution including a thermal acid generator.

The inventors have found that the use of conventional thermal acid generators having high onset temperatures in chemical trimming processes can result in disadvantages such as poor line width roughness (LWR) of the trimmed resist pattern. Use of such conventional thermal acid generators can also be problematic in other materials used in microlithography, for example, in photoresist formulations and in antireflective coatings.

Further improvements in photolithography compositions and processes are needed to achieve the formation of fine patterns in electronic device fabrication and to avoid or conspicuously ameliorate one or more of the foregoing problems associated with the state of the art.

SUMMARY

We have now discovered new ionic thermal acid generators (TAGs) having a low onset temperature. Such TAGs are useful in, e.g., antireflective coating compositions, photoresist compositions, chemical trim overcoat (CTO) compositions, directed self assembly (DSA) patterning schemes, and any other composition in which a lower-temperature TAG would be beneficial.

In one preferred aspect, the invention provides an ionic thermal acid generator represented by the formula:

in which $A^-$ is the anion of an organic or inorganic acid having a pKa of not more than 3; and $(BH)^+$ is the monoprotonated form of a nitrogen-containing base B having a pKa between 0 and 5.0, and a boiling point less than 170° C.

In certain embodiments, B is substituted or unsubstituted pyrimidine, pyrazine, oxazoline, or thiazoline, or difluoromethylammonia, or substituted pyridine, and in further embodiments, B is substituted pyridine (such as 3-fluoropyridine), or substituted or unsubstituted pyrimidine.

In certain embodiments, $A^-$ is the anion of a fluoroalkylsulfonic acid, and in further embodiments, $A^-$ is the anion of a perfluoroalkylsulfonic acid, including perfluorobutanesulfonate. In yet another embodiment, $A^-$ is the anion of an aromatic sulfonic acid, including p-toluenesulfonate.

Substrates such as a semiconductor wafer also are provided having coated thereon a composition of the invention. Other aspects are disclosed infra.

BRIEF DESCRIPTION OF THE DRAWINGS

FIG. 1 is a scheme illustrating chemical trimming of a resist using a chemical trim overcoat (CTO) layer.

DETAILED DESCRIPTION

This invention relates to thermal acid generators (TAGs) and to compositions and methods using TAGs.

It would be advantageous to have TAGs which are capable of producing acid at lower temperatures (e.g., below 100° C.). It has now been found that improvements in line width roughness (LWR) in CTO processes are related to the temperature of the bake (heating) step, with lower bake temperatures generally providing lower (better) LWR values.

In one preferred aspect, the invention provides an ionic thermal acid generator represented by the formula:

in which $A^-$ is the anion of an organic or inorganic acid having a pKa of not more than 3; and $(BH)^+$ is the monoprotonated form of a nitrogen-containing base B having a pKa between 0 and 5.0, and a boiling point less than 170° C.

The group B can advantageously be selected from the group consisting of:

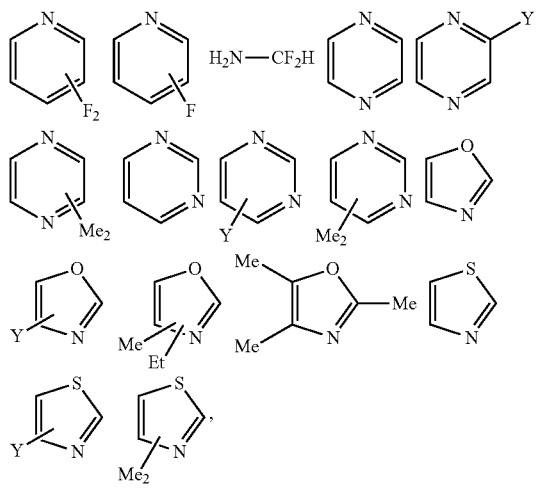

in which Y is methyl or ethyl.

In certain embodiments, B is substituted or unsubstituted pyrimidine, pyrazine, oxazoline, or thiazoline, or difluoromethylammonia, or substituted pyridine, and in further embodiments, B is substituted pyridine (such as 3-fluoropyridine), or substituted or unsubstituted pyrimidine.

In certain embodiments, B is base having a pKa between 0 and 5.0, or between 0 and 4.0, or between 0 and 3.0, or between 1.0 and 3.0. In certain embodiments, B is a nitrogen-containing heteroaromatic base having a pKa between 0 and 5.0, or between 0 and 4.0, or between 0 and 3.0, or between 1.0 and 3.0. As used herein, the term "$pK_a$" is used in accordance with its art-recognized meaning, that is, $pK_a$ is the negative log (to the base 10) of the dissociation constant of the conjugate acid $(BH)^+$ of the basic moiety (B) in aqueous solution at about room temperature. It will be appreciated, however, that the environments in which the TAG compounds of the invention are typically used, namely in organic-based acid-generating compositions, are different than the aqueous solutions in which the above $pK_a$ values are determined. Hence, TAG compounds having a base (B) having $pK_a$ values (for the conjugate acid $(BH)^+$) somewhat outside the above described preferred ranges also may be suitable for purposes of the invention.

In certain embodiments, B is a nitrogen-containing base (including a heteroaromatic base) having a boiling point less than about 170° C., or less than about 160° C., 150° C., 140° C., 130° C., 120° C., 110° C., 100° C., or about 90° C.

In certain embodiments, $A^-$ is the anion of an organic or inorganic acid (AH) having a pKa of not more than about 3, or not more than about 2, or not more than about 1, or not more than 0.0. In certain embodiments, $A^-$ is the anion of an organic acid, such as an alkylsulfonic acid or haloalkylsulfonic acid (e.g., a fluoroalkylsulfonic acid) having 1-8 carbon atoms in the alkyl chain, or 1-4 carbon atoms in the carbon chain, or an arylsulfonic acid. In certain embodiments, $A^-$ is the anion of a fluoroalkylsulfonic acid having 1-4 carbon atoms in the alkyl chain, and in further embodiments, $A^-$ is the anion of a perfluoroalkylsulfonic acid, including perfluorobutanesulfonate. In yet another embodiment, $A^-$ is the anion of an aromatic sulfonic acid, including p-toluenesulfonate.

Advantageously, in certain embodiments, the thermal acid generator can suitably be used at a bake temperature of 100° C. or less, or 90° C. or less, or 80° C. or less, or 70° C. or less, or 60° C. or less.

Preferred TAGs have relatively low molecular weight, for example, a molecular weight of less than or equal to 3000, more preferably ≤2500, ≤2000, ≤1500, ≤1000, ≤800 or even more preferably ≤500.

Specifically preferred TAGs for use in antireflective coating, photoresist, and CTO compositions as disclosed herein include the following:

3-Fluoropyridinium perfluorobutanesulfonate (PFBuS);
3-Fluoropyridinium triflate (OTf); and
3-Fluoropyridinium p-toluenesulfonate (PTSA).

1. Chemical Trim Overcoat (CTO) Compositions

In one aspect, the invention provides a method for providing a photoresist relief image, e.g., by chemical trimming of a relief image to achieve line CDs well below the resolution limit of the imaging tools used for patterning, as well as improved profile and line width roughness, comprising: a) applying a coating layer of a chemical trim overcoat composition comprising an ionic thermal acid generator of the invention over a photoresist relief image in a photoresist layer disposed on a substrate; b) heating the chemical trim overcoat composition layer; and c) developing the photoresist layer.

In another aspect, the invention provides a method for providing a photoresist relief image, comprising: a) applying a coating layer of a chemically amplified photoresist composition on a substrate; b) exposing the photoresist layer to activating radiation and developing the exposed photoresist layer to provide a photoresist relief image; c) applying a coating layer of a chemical trim overcoat composition comprising an ionic thermal acid generator of the invention over the exposed photoresist composition coating layer; d) heating the chemical trim overcoat composition layer; and e) developing the photoresist layer to provide a photoresist relief image.

In certain embodiments, the photoresist composition layer is exposed with patterned radiation having a wavelength of about 248 nm or less, including 193 nm or EUV wavelength (e.g., 13.4 nm).

In still another aspect, the invention provides a coated substrate comprising a photoresist layer; and a chemical trim overcoat layer comprising an ionic thermal acid generator of the invention over the photoresist layer.

The CTO compositions of the invention include a thermal acid generator of the invention and a solvent, and preferably a matrix polymer, and can include additional optional components. When coated over a photoresist pattern formed from a chemically amplified photoresist composition, the CTO compositions can provide various benefits such as controllably reduced resist pattern dimensions and improved process window for the formation of isolated patterns such as isolated lines and posts. The thermally-sensitive component is typically present in the composition in an amount of from about 1-15 wt %, or 2-10 wt %, based on the total solids of the CTO composition.

The matrix polymer allows for the compositions to be coated over the photoresist pattern in the form of a layer having a desired thickness. This will help to ensure the presence of a sufficient content of thermal acid generator for interaction with the photoresist pattern surface.

The matrix polymer should have good solubility in the developer solution to be used in the trimming process. For example, the matrix polymer can be soluble in an aqueous alkaline developer, preferably aqueous quaternary ammonium hydroxide solutions such as aqueous tetramethylammonium hydroxide, or in water. To minimize residue defects originated from the overcoat materials, the dissolution rate of a dried layer of the trimming composition should be greater than that of the photoresist pattern surface region to be removed by the developer solution. The matrix polymer typically exhibits a developer dissolution rate of 100 Å/second or higher, preferably 1000 Å/second or higher. The matrix polymer is soluble in the solvent of the trimming composition, described herein. The matrix polymer can be chosen, for example, from polyvinyl alcohols, polyacrylic acids, polyvinyl pyrrolidones, polyvinyl amines, polyvinyl acetals, poly(meth)acrylates and combinations thereof. Preferably, the polymer contains one or more functional group chosen from —OH, —COOH, —SO$_3$H, SiOH, hydroxyl styrene, hydroxyl naphthalene, sulfonamide, hexafluoroisopropyl alcohol, anhydrates, lactones, esters, ethers, allylamine, pyrolidones and combinations thereof.

The content of the matrix polymer in the composition will depend, for example, on the target thickness of the layer, with a higher polymer content being used for thicker layers. The matrix polymer is typically present in the compositions in an amount of from 80 to 99 wt %, more typically from 90 to 98 wt %, based on total solids of the trimming composition. The weight average molecular weight of the polymer is typically less than 400,000, preferably from (3000) to 50,000, more preferably from 3000 to 25,000.

Polymers useful in the CTO compositions can be homopolymers or can be copolymers having a plurality of distinct repeat units, for example, two, three or four distinct repeat units. The CTO compositions typically include a single polymer, but can optionally include one or more additional polymer. Suitable polymers and monomers for use in the overcoat compositions are commercially available and/or can readily be made by persons skilled in the art.

As described above, a CTO formulation comprising a TAG is overcoated over a pattern in a resist layer (see FIG. 1 for an illustration of this process). Upon heating, the TAG releases acid, which deblocks the surface of the resist layer. Development with an alkaline developer removes the deblocked resist material, resulting in a resist pattern having a greater duty cycle and smaller critical dimension (CD), as well as improved profile and line width roughness.

The CTO compositions of the invention can be used in multiple (i.e., double or higher order) patterning processes, including litho-litho-etch (LLE) double patterning, which involves formation and stabilization of a first lithographic (L1) photoresist pattern followed by formation of a second lithographic (L2) photoresist pattern interdigitated between the L1 pattern. The compositions of the invention can also be used in self-aligned double patterning (SADP), described for example in U.S. Patent Application Pub. No. 2009/0146322A1. In this process, a spacer layer is formed over pre-patterned lines. This is followed by etching to remove all spacer layer material on horizontal surfaces of the lines and spaces, leaving behind only material on the sidewalls of the lines. The original patterned lines are then etched away, leaving behind the sidewall spacers which are used as a mask for etching one or more underlying layers. Since there are two spacers for every line, the line density is effectively doubled.

2. Anti-Reflective Coating Compositions

Reflection of activating radiation used to expose a photoresist often poses limits on resolution of the image patterned in the photoresist layer. Reflection of radiation from the substrate/photoresist interface can produce spatial variations in the radiation intensity in the photoresist, resulting in non-uniform photoresist linewidth upon development. Radiation also can scatter from the substrate/photoresist interface into regions of the photoresist where exposure is non intended, again resulting in linewidth variations. The amount of scattering and reflection will typically vary from region to region, resulting in further linewidth non-uniformity. Variations in substrate topography also can give rise to resolution-limiting problems.

One approach used to reduce the problem of reflected radiation has been the use of a radiation absorbing layer interposed between the substrate surface and the photoresist coating layer. See for example, PCT Application WO 90/03598, EPO Application No. 0 639 941 A1 and U.S. Pat. Nos. 4,910,122, 4,370,405, 4,362,809, and 5,939,236. Such layers have also been referred to as antireflective layers or antireflective compositions. See also U.S. Pat. Nos. 5,939,236; 5,886,102; 5,851,738; and 5,851,730, which disclose highly useful antireflective compositions. In one aspect, an antireflective composition for use with an overcoated photoresist is provided. The antireflective coating composition comprises an ionic thermal acid generator of the invention and a resin. In a further aspect, the invention provides a coated substrate comprising an antireflective composition layer comprising the antireflective coating composition of the invention. In a still further aspect, the invention provides a coated substrate comprising an antireflective composition layer comprising an antireflective coating composition of the invention; and a photoresist layer coated over the antireflective composition layer.

Exemplary resin components for use in antireflective coatings are known in the art. See, e.g., U.S. Pat. No. 6,852,421 to Wayton et al. Antireflective coating compositions of the invention preferably are crosslinking compositions and contain a material that will crosslink or otherwise cure upon e.g. thermal or activating radiation treatment. Typically, the composition will contain a crosslinker component, e.g. an amine-containing material such as a melamine or benzoguanamine compound or resin.

Preferably, crosslinking antireflective compositions of the invention can be cured through thermal treatment of the composition coating layer. Suitably, the coating composition also contains a thermal acid generator compound of the invention (and, optionally, one or more additional conventional TAGs), to facilitate the crosslinking reaction.

For use as an antireflective coating composition, as well as other applications such as via-fill, preferably the composition is crosslinked prior to applying a photoresist composition layer over the composition layer.

Antireflective compositions of the invention also preferably contain a component that comprises chromophore groups that can absorb undesired radiation used to expose the overcoated resist layer from reflecting back into the resist layer. Such chromophore groups may be present with other composition components such as the polyester resin or an acid generator compound, or the composition may comprise another component that may comprise such chromophore units, e.g. a resin separate from the polyester resin that contains chromophore substitution, or a small molecule (e.g. MW less than about 1000 or 500) that contains one or more chromophore moieties, such as one or more optionally substituted phenyl, optionally substituted anthracene or optionally substituted naphthyl groups.

Generally preferred chromophores for inclusion in antireflective coating compositions of the invention particularly those used for antireflective applications include both single ring and multiple ring aromatic groups such as optionally substituted phenyl, optionally substituted naphthyl, optionally substituted anthracenyl, optionally substituted phenanthracenyl, optionally substituted quinolinyl, and the like. Particularly preferred chromophores may vary with the radiation employed to expose an overcoated resist layer. More specifically, for exposure of an overcoated resist at 248 nm, optionally substituted anthracene and optionally substituted naphthyl are preferred chromophores of the antireflective composition. For exposure of an overcoated resist at 193 nm, optionally substituted phenyl and optionally substituted naphthyl are particularly preferred chromophores of the antireflective composition. Preferably, such chromophore groups are linked (e.g. pendant groups) to a resin component of the antireflective composition, such as the polyester resin as discussed above.

As discussed above, the antireflective coating compositions of the invention include one or more thermal acid generators (TAGs) of the invention. An antireflective coating composition may optionally further comprise one or more conventional TAGs as discussed below.

A conventional TAG can generate a strong acid such as a sulfonic acid upon exposure to heat. The acid can be aromatic or non-aromatic. Suitable conventional TAGs can be activated at a temperature greater than 50° C., for example, greater than 70° C., greater than 90° C., greater than 120° C. or greater than 150° C. Suitable TAGs are chosen from those which generate aromatic or non-aromatic acids, with or without fluorine substitution. Examples of suitable thermal acid generators include nitrobenzyl tosylates, such as 2-nitrobenzyl tosylate, 2,4-dinitrobenzyl tosylate, 2,6-dinitrobenzyl tosylate, 4-nitrobenzyl tosylate; benzenesulfonates such as 2-trifluoromethyl-6-nitrobenzyl 4-chlorobenzenesulfonate, 2-trifluoromethyl-6-nitrobenzyl 4-nitro benzenesulfonate; phenolic sulfonate esters such as phenyl, 4-methoxybenzenesulfonate; alkyl ammonium salts of organic acids, such as triethylammonium salt of 10-camphorsulfonic acid, trifluoromethylbenzenesulfonic acid, perfluorobutane sulfonic acid; and particular onium salts. A variety of aromatic (anthracene, naphthalene or benzene derivatives) sulfonic acid amine salts can be employed as the TAG, including those disclosed in U.S. Pat. Nos. 3,474,054, 4,200,729, 4,251,665 and 5,187,019. Typically conventional TAGs have a very low volatility at temperatures between 170 and 220° C. Examples of TAGs include those sold by King Industries, Norwalk, Conn. USA under NACURE™, CDX™ and K-PURE™ names, for example, NACURE 5225, CDX-2168E, K-PURE™ 2678 and K-PURE™ 2700.

Antireflective coating compositions of the invention are typically formulated and applied to a substrate as an organic solvent solution, suitably by spin-coating (i.e. a spin-on composition). As discussed above, in a preferred aspect, compositions of the invention are formulated with a solvent component that comprises one or more oxyisobutyric acid esters, particularly methyl-2-hydroxyisobutyrate. Especially preferred coating compositions of the invention include a polyester resin, particularly having ester repeat units as a component of the polymer backbone, and formulated with a solvent component that comprises one or more oxyisobutyric acid esters such as methyl-2-hydroxyisobutyrate.

A variety of photoresists may be used in combination (i.e., overcoated) with a coating composition of the invention. Preferred photoresists for use with the antireflective compositions of the invention are chemically-amplified resists, especially positive-acting photoresists that contain one or more photoacid generator compounds and a resin component that contains units that undergo a deblocking or cleavage reaction in the presence of photogenerated acid, such as photoacid-labile ester, acetal, ketal or ether units. Negative-acting photoresists also can be employed with coating compositions of the invention, such as resists that crosslink (i.e. cure or harden) upon exposure to activating radiation. Preferred photoresists for use with a coating composition of the invention may be imaged with relatively short-wavelength radiation, e.g. radiation having a wavelength of less than 300 nm or less than 260 nm such as about 248 nm, or radiation having a wavelength of less than about 200 nm or less than about 170 nm, such as about 193 nm or 157 nm.

As discussed above, antireflective compositions may suitably contain an additional resin component. Suitable resin components may contain chromophore units for absorbing radiation used to image an overcoated resist layer before undesired reflections can occur.

For deep UV applications (i.e. the overcoated resist is imaged with deep UV radiation), a polymer of an antireflective composition preferably will absorb reflections in the deep UV range (typically from about 100 to 300 nm). Thus, the polymer preferably contains units that are deep UV chromophores, i.e. units that absorb deep UV radiation. Highly conjugated moieties are generally suitable chromophores, such as anthracene, naphthyl and phenyl.

3. Photoresist Compositions

In a preferred aspect, photoresist compositions are provided that comprise a resin, a photoacid generator, and one or more thermal acid generators (TAGs), including at least one TAG of the invention, and optionally a basic component (or "quencher").

TAGs can be used as photospeed enhancers for photoresist compositions. For certain photoresist compositions and methods, such as photoresist compositions for exposure with a KrF light source (at 248 nm) and methods of using such photoresist compositions, the lower-temperature TAGs of the invention can provide improved photospeed compared to conventional higher-temperature TAGs.

In one embodiment, the invention provides a photoresist formulation comprising: (a) a resin; (b) a photoacid generator; and (c) an ionic thermal acid generator of the invention. In certain embodiments, the photoresist formulation further comprises (d) a basic component (quencher) present in equivalent excess relative to the thermal acid generator.

Preferably, thermal acid generators and basic compounds (quenchers) of the invention are used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions. Ester groups that contain a tertiary non-cyclic alkyl carbon or a tertiary alicyclic carbon covalently linked to the carboxyl oxygen of the ester are generally preferred photoacid-labile groups of resins employed in photoresists of the invention. Acetal groups also are suitable photoacid-labile groups.

Photoresists of the invention typically comprise a resin binder (polymer), a photoactive component such as one or more photoacid generators, and at least one Tag and at least one quencher as disclosed herein. Preferably the resin binder has functional groups that impart alkaline aqueous developability to the photoresist composition. For example, preferred are resin binders that comprise polar functional groups such as hydroxyl or carboxylate. Preferably the resin binder is used in a resist composition in an amount sufficient to render the resist developable with an aqueous alkaline solution.

Preferred imaging wavelengths of the photoresists of the invention include sub-300 nm wavelengths, such as 248 nm, and more preferably sub-200 nm wavelengths, such as 193 nm or EUV wavelength (e.g., 13.4 nm).

Particularly preferred photoresists of the invention may be used in immersion lithography applications. See, for example, U.S. Pat. No. 7,968,268 to Rohm and Haas Electronic Materials for a discussion of preferred immersion lithography photoresists and methods. Preferred photoresists for use in immersion application may comprise a resin (which may be fluorinated and/or have photoacid-labile groups) that is separate (not covalently linked) and distinct from a primary resin that has photoacid-labile groups. Thus, the present invention includes in preferred aspects photoresists that comprise: 1) a first resin with photoacid-labile groups; 2) one or more photoacid generator compounds; 3) a second resin that is separate and distinct from the first resin, the second resin may be fluorinated and/or have photoacid-acid groups; and 4) one or more TAGs and one or more quenchers as disclosed herein.

Particularly preferred photoresists of the invention contain an imaging-effective amount of one or more PAGs and one or more TAGs as disclosed herein and a resin that is selected from the group of:

1) a phenolic resin that contains acid-labile groups that can provide a chemically amplified positive resist particularly suitable for imaging at 248 nm. Particularly preferred resins of this class include: i) polymers that contain polymerized units of a vinyl phenol and an alkyl (meth)acrylate, where the polymerized alkyl (meth)acrylate units can undergo a deblocking reaction in the presence of photoacid. Exemplary alkyl (meth)acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic (meth)acrylates that can undergo a photoacid-induced reaction, such as polymers in U.S. Pat. Nos. 6,042,997 and 5,492,793, incorporated herein by reference; ii) polymers that contain polymerized units of a vinyl phenol, an optionally substituted vinyl phenyl (e.g., styrene) that does not contain a hydroxy or carboxy ring substituent, and an alkyl (meth)acrylate such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups.

2) a resin that is substantially or completely free of phenyl groups that can provide a chemically amplified positive resist particularly suitable for imaging at sub-200 nm wavelengths such as 193 nm. Particularly preferred resins of this class include: i) polymers that contain polymerized units of a non-aromatic cyclic olefin (endocyclic double bond) such as an optionally substituted norbornene, such as polymers described in U.S. Pat. No. 5,843,624; ii) polymers that contain alkyl (meth)acrylate units such as e.g. t-butyl acrylate, t-butyl methacrylate, methyladamantyl acrylate, methyl adamantyl methacrylate, and other non-cyclic alkyl and alicyclic (meth)acrylates; such polymers have been described in U.S. Pat. No. 6,057,083. Polymers of this type may contain in preferred aspects certain aromatic groups such as hydroxynaphthyl.

Preferred resins for use in photoresists to be imaged at sub-200 nm, such as at 193 nm, comprises units of two or more of the following general formulae (I), (II) and (III):

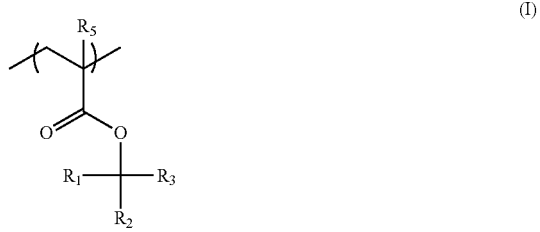

(I)

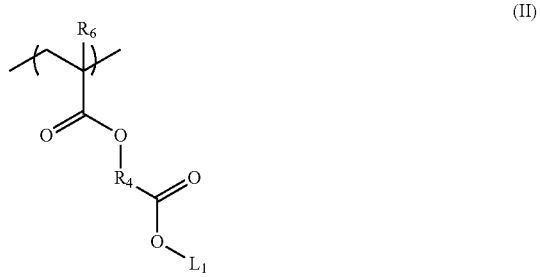

(II)

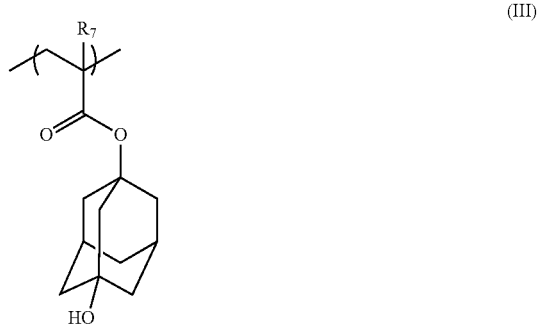

(III)

wherein: $R_1$, R2 and R3 are each optionally substituted $(C_1-C_{30})$alkyl group; $R_1$, $R_2$ and $R_3$ may connect to form a ring; $R_4$ is a $(C_1-C_3)$alkylene group; $L_1$ is a lactone group; and $R_5$, $R_6$ and $R_7$ are each hydrogen, fluorine, (C1-C4)alkyl and (C1-C4)fluoroalkyl.

The unit of general formula (I) includes an acid labile group that undergoes a photoacid-promoted deprotection reaction on exposure to activating radiation and heat treatment. This allows for a switch in polarity of the matrix polymer, leading to a change in solubility of the polymer and photoresist composition in an organic developer. Suitable monomers for forming units of formula (I) include, for example, the following:

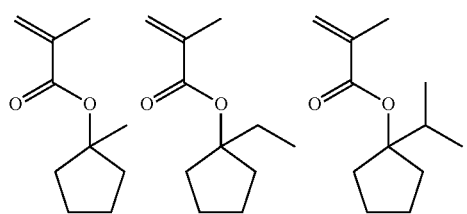

-continued

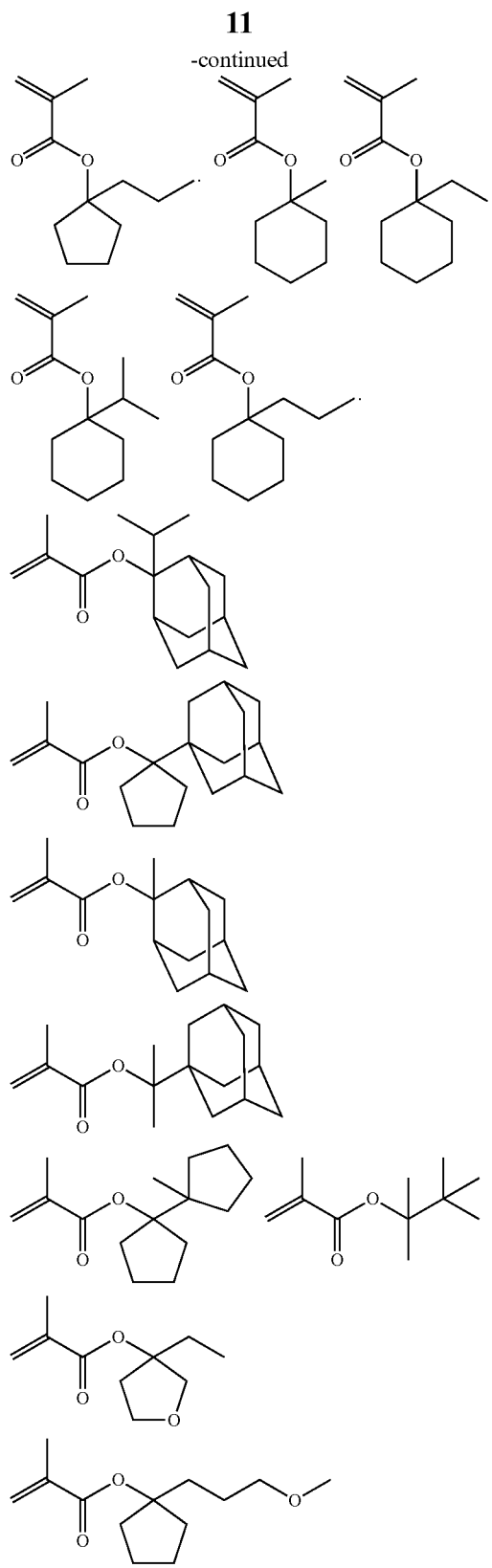

The unit of general formula (II) includes a lactone moiety effective to control the dissolution rate of the matrix polymer and photoresist composition. Suitable monomers for forming units of general formula (II) include, for example, the following:

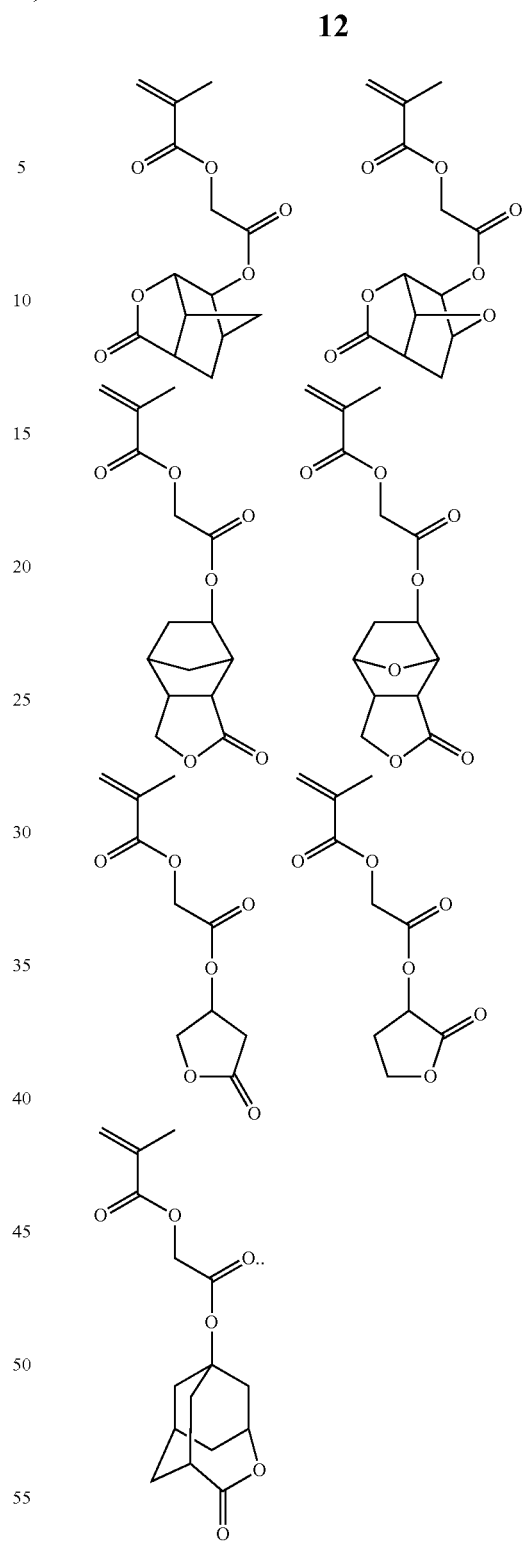

The unit of formula (III) provides a polar group, which enhances etch resistance of the resin and photoresist composition and provides additional means to control the dissolution rate of the resin and photoresist composition. Monomers for forming the unit of formula (III) include 3-hydroxy-1-adamantyl methacrylate (HAMA) and preferably 3-hydroxy-1-adamantyl acrylate (HADA).

The resin can include one or more additional units of general formulae (I), (II) and/or (III) different from the first units. Where additional such units are present in the resin, they will preferably include an additional leaving group-containing unit of formula (I) and/or a lactone-containing unit of formula (II).

In addition to the polymerized units described above, the resin can include one or more additional units which are not of general formula (I), (II) or (III). For example, a particularly suitable lactone group-containing unit is of the following general formula (IV):

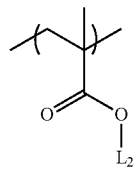

(IV)

wherein: $L_2$ is a lactone group; and the unit of general formula (IV) is different from the unit of general formula (II). The following exemplary monomers are suitable for use in forming the additional lactone unit of general formula (IV):

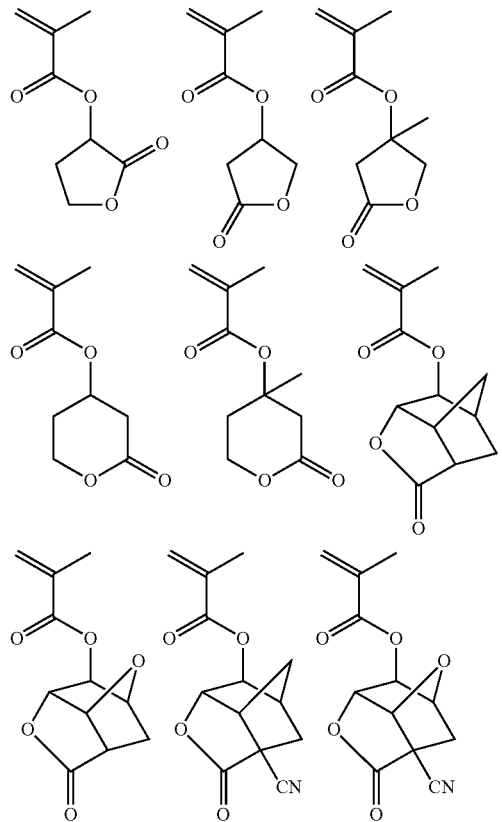

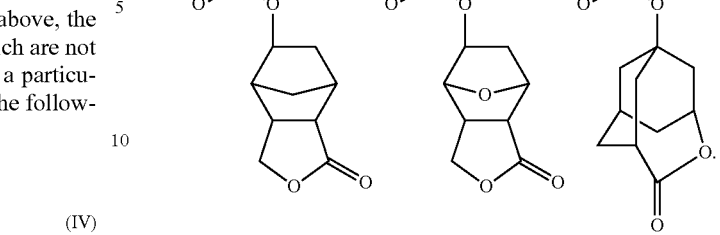

Preferably, $L_1$ in the unit of general formula (II) and $L_2$ in the unit of general formula (IV) are independently chosen from the following lactone groups:

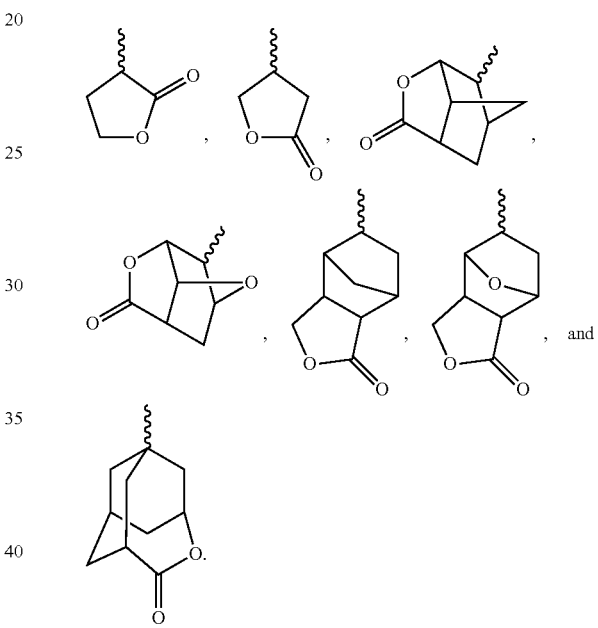

Typically, the additional units for the resin will include the same or similar polymerizable group as those used for the monomers used to form the units of general formula (I), (II) or (III), but may include other, different polymerizable groups in the same polymer backbone, such as those which contain polymerized units of vinyl or a non-aromatic cyclic olefin (endocyclic double bond) such as an optionally substituted norbornene. For imaging at sub-200 nm wavelengths such as 193 nm, the resin is typically substantially free (that is, less than 15 mole %) of phenyl, benzyl or other aromatic groups where such groups are highly absorbing of the radiation. Suitable additional monomeric units for the polymer include, for example, one or more of the following: monomeric units containing ethers, lactones or esters, such as 2-methyl-acrylic acid tetrahydro-furan-3-yl ester, 2-methyl-acrylic acid 2-oxo-tetrahydro-furan-3-yl ester, 2-methyl-acrylic acid 5-oxo-tetrahydro-furan-3-yl ester, 2-methyl-acrylic acid 3-oxo-4,10-dioxa-tricyclo[5.2.1.02,6] dec-8-yl ester, 2-methyl-acrylic acid 3-oxo-4-oxa-tricyclo [5.2.1.02,6]dec-8-yl ester, 2-methyl-acrylic acid 5-oxo-4-oxa-tricyclo[4.2.1.03,7]non-2-yloxycarbonylmethyl ester, acrylic acid 3-oxo-4-oxa-tricyclo[5.2.1.02,6]dec-8-yl ester, 2-methyl-acrylic acid 5-oxo-4-oxa-tricyclo[4.2.1.03,7]non- 2-yl ester, and 2-methyl-acrylic acid tetrahydro-furan-3-yl ester; monomeric units having polar groups such as alcohols and fluorinated alcohols, such as 2-methyl-acrylic acid 3-hydroxy-adamantan-1-yl ester, 2-methyl-acrylic acid 2-hydroxy-ethyl ester, 6-vinyl-naphthalen-2-ol, 2-methyl-acrylic acid 3,5-dihydroxy-adamantan-1-yl ester, 2-methyl-acrylic acid 6-(3,3,3-trifluoro-2-hydroxy-2-trifluoromethyl-propyl)-bicyclo[2.2.1]hept-2-yl, and 2-bicyclo[2.2.1]hept-5-en-2-ylmethyl-1,1,1,3,3,3-hexafluoro-propan-2-ol; monomeric units having acid labile moieties, for example, ester groups that contain a tertiary non-cyclic alkyl carbon such as t-butyl, or a tertiary alicyclic carbon such as methyladamantyl or ethylfenchyl covalently linked to a carboxyl oxygen of an ester of the polymer, 2-methyl-acrylic acid 2-(1-ethoxy-ethoxy)-ethyl ester, 2-methyl-acrylic acid 2-ethoxymethoxy-ethyl ester, 2-methyl-acrylic acid 2-methoxymethoxy-ethyl ester, 2-(1-ethoxy-ethoxy)-6-vinyl-naphthalene, 2-ethoxymethoxy-6-vinyl-naphthalene, and 2-methoxymethoxy-6-vinyl-naphthalene. The additional units if used are typically present in the polymer in an amount of from 10 to 30 mol %.

Exemplary preferred resins include, for example, the following:

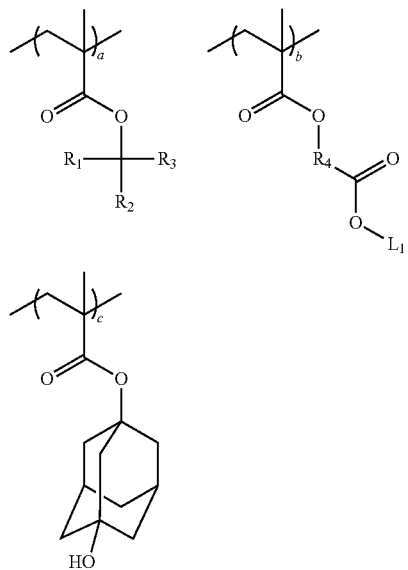

wherein: 0.3<a<0.7; 0.3<b<0.6; and 0.1<c<0.3;

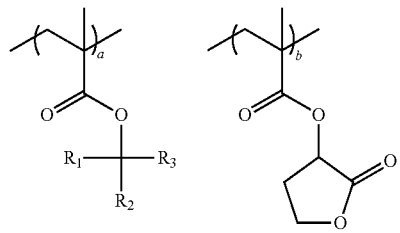

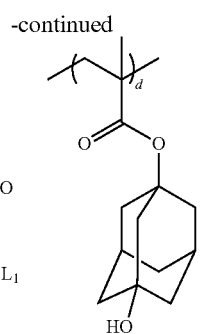

wherein: 0.3<a<0.7; 0.1<b<0.4; 0.1<c<0.4, and 0.1<d<0.3.

Blends of two or more resins can be used in the compositions of the invention. The resin is present in the resist composition in an amount sufficient to obtain a uniform coating of desired thickness. Typically, the resin is present in the composition in an amount of from 70 to 95 wt % based on total solids of the photoresist composition. Because of improved dissolution properties of the resin in organic developers, useful molecular weights for the resin are not limited to lower values, but cover a very broad range. For example, the weight average molecular weight $M_w$ of the polymers is typically less than 100,000, for example, from 5000 to 50,000, more typically from 6000 to 30,000 or from 7,000 to 25,000.

Suitable monomers used in forming the resins are commercially available and/or can be synthesized using known methods. The resins can readily be synthesized by persons skilled in the art using the monomers with known methods and other commercially available starting materials.

Photoresists of the invention also may comprise a single PAG or a mixture of distinct PAGs, typically a mixture of 2 or 3 different PAGs, more typically a mixture that consists of a total of 2 distinct PAGs. The photoresist composition comprises a photoacid generator (PAG) employed in an amount sufficient to generate a latent image in a coating layer of the composition upon exposure to activating radiation. For example, the photoacid generator will suitably be present in an amount of from 1 to 20 wt % based on total solids of the photoresist composition. Typically, lesser amounts of the PAG will be suitable for chemically amplified resists as compared with non-chemically amplified materials.

Suitable PAGs are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4- methoxyphenyl)-4,6-bis(trichloromethyl)-1,3,5-triazine, and 2-(4-methoxynaphthyl)-4,6-bis(trichloromethyl)-1,3,5-triazine.

Photoresists of the invention comprise one or more TAGs as disclosed herein suitably with a wide amount range. For example, the TAG can be present in an amount such as from 0.005 to 15 wt %, based on the weight of the PAG, preferably from 0.01 to 15 wt %, and even more preferably from 0.01 to 10 wt %. The TAG is suitably used in amounts of 0.01, 0.05, 0.1, 0.02, 0.3, 0.4, 0.5 or 1 to 10 or 15 wt % relative to the PAG, and more typically amounts of 0.01, 0.05, 0.1, 0.02, 0.3, 0.4, 0.5 or 1 to 5, 6, 7, 8, 9 or 10 weight percent. A photoresist composition may optionally further comprise one or more conventional TAGs as discussed above for antireflective coating compositions.

The present photoresist compositions typically comprise a solvent. Suitable solvents include, for example: glycol ethers such as 2-methoxyethyl ether (diglyme), ethylene glycol monomethyl ether, and propylene glycol monomethyl ether; propylene glycol monomethyl ether acetate; lactates such as methyl lactate and ethyl lactate; propionates such as methyl propionate, ethyl propionate, ethyl ethoxy propionate and methyl-2-hydroxy isobutyrate; Cellosolve esters such as methyl Cellosolve acetate; aromatic hydrocarbons such as toluene and xylene; and ketones such as acetone, methylethyl ketone, cyclohexanone and 2-heptanone. A blend of solvents such as a blend of two, three or more of the solvents described above also are suitable. The solvent is typically present in the composition in an amount of from 90 to 99 wt %, more typically from 95 to 98 wt %, based on the total weight of the photoresist composition.

The photoresist compositions can also include other optional materials. For example, the compositions can include one or more of actinic and contrast dyes, antistriation agents, plasticizers, speed enhancers, sensitizers, and the like. Such optional additives if used are typically present in the composition in minor amounts such as from 0.1 to 10 wt % based on total solids of the photoresist composition.

The photoresists of the invention are generally prepared following known procedures. For example, a photoresist composition of the invention can be prepared by dissolving the components of the photoresist in a suitable solvent. The resin binder component of photoresists resists of the invention are typically used in an amount sufficient to render an exposed coating layer of the resist developable such as with an aqueous alkaline solution. More particularly, a resin binder will suitably comprise 50 to 90 weight percent of total solids of the resist. The photoactive component should be present in an amount sufficient to enable generation of a latent image in a coating layer of the resist. More specifically, the photoactive component will suitably be present in an amount of from 1 to 40 weight percent of total solids of a photoresist. Typically, lesser amounts of the photoactive component will be suitable for chemically amplified resists.

The desired total solids content of the present photoresist compositions will depend on factors such as the particular polymers in the composition, final layer thickness and exposure wavelength. Typically the solids content of the photoresist varies from 1 to 10 wt %, more typically from 2 to 5 wt %, based on the total weight of the photoresist composition.

Preferred negative-acting compositions of the invention comprise a mixture of materials that will cure, crosslink or harden upon exposure to acid, and a photoactive component of the invention. Particularly preferred negative acting compositions comprise a resin binder such as a phenolic resin, a crosslinker component and a photoactive component of the invention. Such compositions and the use thereof has been disclosed in European Patent Applications 0164248 and 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins are sold under the trade names Cymel 1123 and 1125.

If a quencher is present, any known quencher can be used. Known quenchers include those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, 1,1',1"-nitrilotripropan-2-ol, 1,1',1"',1"'-(ethane-1,2-diylbis(azanetriyl))tetrapropan-2-ol, aryl amines such as diphenylamine, triphenylamine, aminophenol, and 2-(4-aminophenyl)-2-(4-hydroxyphenyl)propane, Troger's base, a hindered amine such as diazabicycloundecene (DBU) or diazabicyclononene (DBN), amides like tert-butyl 1,3-dihydroxy-2-(hydroxymethyl)propan-2-ylcarbamate and tert-butyl 4-hydroxypiperidine-1-carboxylateor; or ionic quenchers including quaternary alkyl ammonium salts such as tetrabutylammonium hydroxide (TBAH) or tetrabutylammonium lactate.

Preferred quenchers for use in photoresists may be polymeric or non-polymeric, with non-polymeric quenchers preferred for many applications. Preferred quenchers have relatively low molecular weight, for example, a molecular weight of less than or equal to 3000, more preferably ≤2500, ≤2000, ≤1500, ≤1000, ≤800 or even more preferably ≤500.

Preferred quenchers include basic compounds capable of reacting with a thermally-generated acid from a TAG. Suitable quenchers are known in the art and include compounds such as amines, including polyamines, such as diamines, triamines, or tetraamines, as well as quaternary ammonium compounds, trialkylammonium compounds, amides, ureas, TBOC-blocked amines, and the like.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image. The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also suitably employed, for example, glass substrates, indium tin oxide coated substrates and the like. A liquid coating resist composition may be applied by any standard means such as spinning, dipping or roller coating.

The exposure energy should be sufficient to effectively activate the photoactive component of the radiation sensitive system to produce a patterned image in the resist coating layer. Suitable exposure energies typically range from 1 to 300 mJ/cm$^2$. As discussed above, preferred exposure wavelengths include sub-200 nm such as 193 nm.

The photoresist layer (with overcoated barrier composition layer, if present) may be preferably exposed in an immersion lithography system, i.e. where the space between the exposure tool (particularly the projection lens) and the photoresist coated substrate is occupied by an immersion fluid, such as water or water mixed with one or more additives such as cesium sulfate which can provide a fluid of enhanced refractive index. Preferably the immersion fluid (for example, water) has been treated to avoid bubbles, for example water can be degassed to avoid nanobubbles.

References herein to "immersion exposing" or other similar term indicates that exposure is conducted with such a fluid layer (for example, water or water with additives) interposed between an exposure tool and the coated photoresist composition layer.

After exposure, a thermal treatment is typically employed for chemically-amplified photoresists. Suitable post-exposure bake temperatures are from about 50° C. or greater, more specifically from 50 to 140° C. For an acid-hardening negative-acting resist, a post-development bake may be employed if desired at temperatures of from 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

The invention also provide methods for forming relief images of the photoresists of the invention, including methods for forming highly resolved patterned photoresist images (for example, a patterned line having essentially vertical sidewalls) of sub-quarter μm dimensions or less, such as sub-0.2 or sub-0.1 μm dimensions.

The invention further provides articles of manufacture comprising substrates such as a microelectronic wafer or a flat panel display substrate having coated thereon the photoresists and relief images of the invention.

Example 1

Resist Example (Resist A)

A positive chemically amplified photoresist composition (Resist A) was prepared by combining 1.28 g Polymer A (M1/M2/M3=4/4/2 mole ratio, Mw=10K) and 1.28 g Polymer B (M1/M2/M3/M4=30/35/15/20, Mw=7K),

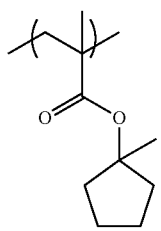

M1

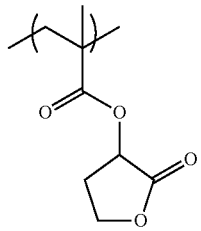

M2

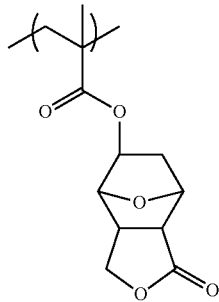

M3

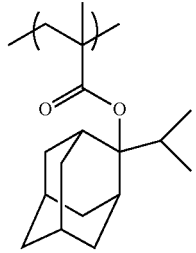

M4

0.56 g photoacid generator of 4-(t-butylphenyl)tetramethylenesulfonium 4-(adamantane-1-carbonyloxy)-1,1,2,2-tetrafluorobutane sulfonate (TMS-Ad-TFBS), 0.078 g quencher of Trihydroxymethyl-carbamic acid tert-butyl ester, 0.003 g POLYFOX 656 surfactant, 33.56 g propylene glycol methyl ether acetate and 63.25 g methyl-2-hydroxy-iso-butyrate.

Example 2

Coating and Processing of Resist

Resist A (Example 1) was spin coated on organic bottom antireflective coating (BARC AR124 23 nm/AR26N 77 nm) over 12 inch silicon wafers and softbaked at 95° C./60 sec. Then 30 nm OC2000 topcoat (from Dow Chemical Company) was applied on the resist. The coated wafer was exposed on ASML ArF 1900i with NA=1.30, Dipole 35Y illumination (0.9/0.635sigma), plus x polarization, and then post-exposure baked at 80° C./60 sec. The coated wafers were then treated with 0.26N (normal) aqueous tetramethylammonium hydroxide solution to develop a 45 nm 1:1 line and space pattern imaged resist layer.

Example 3

Chemical Trim Overcoat Composition (CTO1)

2.318 g copolymer of t-butyl acrylate/methacrylic acid (7/3 of mole ratio), 0.132 g of 3-Fluoropyridinium perfluorobutanesulfonate, 19.51 g decane and 78.04 g 2-methyl-1-butynol were mixed until all components dissolve and then filtered by 0.2 um Nylon filter. A 60 nm film of CTO1 was spin-coated on resist with 45 nm 1:1 line and space patterns, baked at 70° C., and developed in 2.38% TMAH developer for 12 s with TEL Lithus GP nozzle.

Example 4

Chemical Trim Overcoat Composition (CTO2)

2.324 g copolymer of t-butyl acrylate/methacrylic acid (7/3 of mole ratio), 0.126 g of Pyridinium perfluorobutanesulfonate, 19.51 g decane and 78.04 g 2-methyl-1-butynol were mixed until all components dissolved and then filtered by 0.2 um Nylon filter. A 60 nm film of CTO2 was spin-coated on resist with 45 nm 1:1 line and space patterns, baked at 70° C. and developed in 2.38% TMAH developer for 12 s with TEL Lithus GP nozzle.

Example 5

CTO Comparative Example (for Comparison with CTO1)

2.323 g copolymer of t-butyl acrylate/methacrylic acid (7/3 of mole ratio), 0.127 g of Pyridazinium perfluorobutanesulfonate, 19.51 g decane and 78.04 g 2-methyl-1-butynol were mixed until all components dissolve and then filtered by 0.2 um Nylon filter. A 60 nm film of CTO1 (Example 3) was spin-coated on resist with 45 nm 1:1 line and space patterns, baked at 70° C. and developed in 2.38% TMAH developer for 12 s with TEL Lithus GP nozzle.

Example 6

CTO Comparative Example (for Comparison with CTO2)

2.344 g copolymer of t-butyl acrylate/methacrylic acid (7/3 of mole ratio), 0.106 g of Ammonium perfluorobutanesulfonate, 19.51 g decane and 78.04 g 2-methyl-1-butynol were mixed until all components dissolve and then filtered by 0.2 um Nylon filter. A 60 nm film of CTO2 was spin-coated on resist with 45 nm 1:1 line and space patterns, baked at 70° C. and developed in 2.38% TMAH developer for 12 s with TEL Lithus GP nozzle.

Results are set forth in Table 1.

TABLE 1

| TAG | CTO | b.p. (base) | pKa (base) | Final CD | ΔCD |
|---|---|---|---|---|---|
| No CTO | NA | NA | NA | 45.7 nm | NA |
| 3-Fluoropyridinium PFBuS | CTO 1 | 108° C. | 2.8 | 26.4 nm | 19.3 nm |
| Pyridinium PFBuS | CTO 2 | 115° C. | 5.14 | 34.3 nm | 11.5 nm |
| Pyridazinium PFBuS | Comparative CTO 1 | 208° C. | 3.1 | 40.6 nm | 5.1 nm |
| Ammonium PFBuS | Comparative CTO 2 | -33° C. | 9.25 | 45.8 nm | -0.1 nm |

The CD shrink values shown in Table 1 confirm that the CTO composition with an ammonium TAG (Example 6) exhibits no CD shrink at this temperature, whereas the pyridinium TAG (CTO2) shows 11.5 nm shrink. Without wishing to be bound by theory, it is believed that the lack of CD shrink in the composition with the ammonium TAG is due to the high pKa of ammonia (9.25), whereas the pyridinium TAG of Example 5 has a lower pKa. The 3-fluoropyridinium TAG (CTO1, Example 3) shows an even greater CD shrink than the pyridinium TAG, and, without wishing to be bound by theory, it is believed that this is due, at least in part, to the lower pKa of 3-fluoropyridine vs. pyridine (at similar boiling point).

Comparative Example 5 uses a TAG made from pyridazine, a base with a pKa similar to that of 3-fluoropyridine, but a 100° C. higher boiling point. As shown in Table 1, the pyridazinium TAG results in relatively small shrink.

What is claimed is:

1. A method for providing a photoresist relief image, comprising:
   a) applying a coating layer of a chemically amplified photoresist composition on a substrate;
   b) exposing the photoresist layer to activating radiation and developing the exposed photoresist layer to provide a photoresist relief image;
   c) applying over the exposed photoresist composition coating layer a coating layer of a chemical trim overcoat composition comprising a thermal acid generator of formula (I);

$$(A^-)(BH)^+ \tag{I}$$

in which
   A⁻ is the anion of an organic or inorganic acid having a pKa of not more than 3; and
   (BH)⁺ is the monoprotonated form of a nitrogen-containing base B having a pKa between 0 and 5.0, and a boiling point less than 170° C.;
   d) heating the chemical trim overcoat composition layer; and
   e) developing the photoresist layer to provide a photoresist relief image.

2. The method of claim 1 wherein B is selected from the group consisting of:

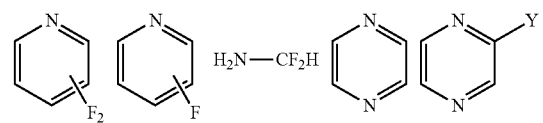

-continued

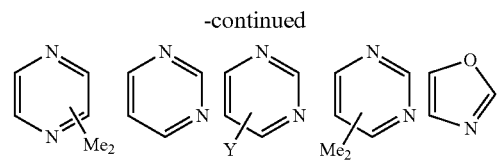

-continued

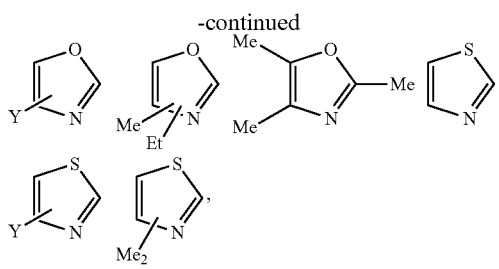

in which Y is methyl or ethyl.

3. The method of claim 1 wherein B is substituted pyridine.

4. The method of claim 1 wherein A⁻ is the anion of a fluoroalkylsulfonic acid.

5. The method of claim 1 wherein the thermal acid generator is selected from among:
3-Fluoropyridinium perfluorobutanesulfonate;
3-Fluoropyridinium triflate; and
3-Fluoropyridinium p-toluenesulfonate.

6. A coated substrate comprising:
a photoresist layer; and
over the photoresist layer, a chemical trim overcoat layer comprising an ionic thermal acid generator of formula (I)

in which
A⁻ is the anion of an organic or inorganic acid having a pKa of not more than 3; and
(BH)⁺ is the monoprotonated form of a nitrogen-containing base B having a pKa between 0 and 5.0, and a boiling point less than 170° C.

7. The substrate of claim 6 wherein B is selected from the group consisting of:

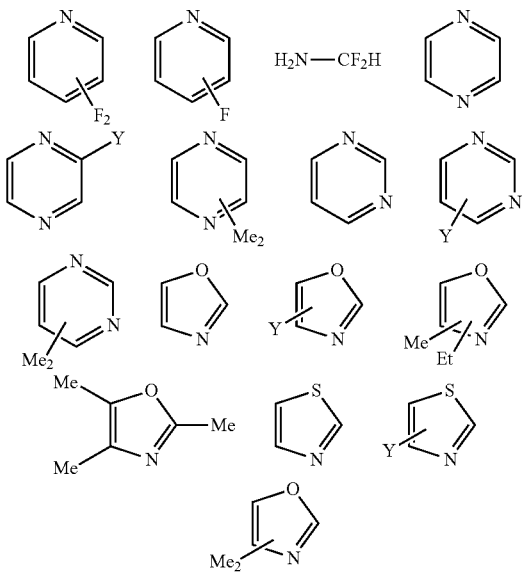

in which Y is methyl or ethyl.

8. The substrate of claim 6 wherein B is substituted pyridine.

9. The substrate of claim 6 wherein A⁻ is the anion of a fluoroalkylsulfonic acid.

10. The substrate of claim 6 wherein the thermal acid generator is selected from among:
3-Fluoropyridinium perfluorobutanesulfonate;
3-Fluoropyridinium triflate; and
3-Fluoropyridinium p-toluenesulfonate.

11. A coated substrate comprising: an antireflective composition layer comprising a thermal acid generator of formula (I):

in which A⁻ is the anion of an organic or inorganic acid having a pKa of not more than 3; and (BH)⁺ is the monoprotonated form of a nitrogen-containing base B having a pKa between 0 and 5.0, and a boiling point less than 170° C.;
and over the antireflective coating composition layer, a photoresist composition layer, wherein B is selected from the group consisting of:

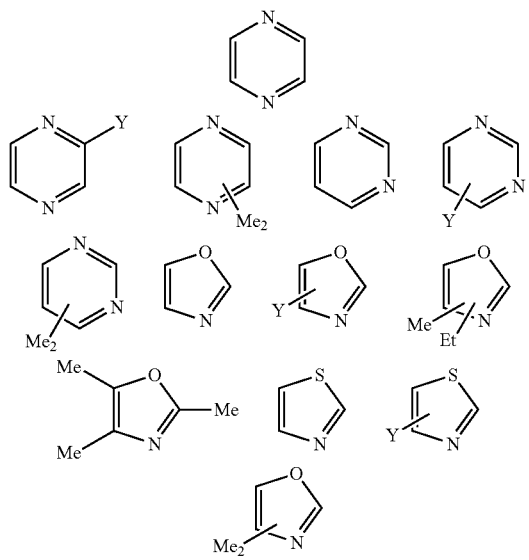

and substituted pyridine,
in which Y is methyl or ethyl.

12. The substrate of claim 11 wherein B is substituted pyridine.

13. The substrate of claim 11 wherein A⁻ is the anion of a fluoroalkylsulfonic acid.

14. The substrate of claim 11 wherein the thermal acid generator is selected from among:
3-Fluoropyridinium perfluorobutanesulfonate;
3-Fluoropyridinium triflate; and
3-Fluoropyridinium p-toluenesulfonate.

15. A thermal acid generator represented by the formula:

in which
A⁻ is the anion of a fluoroalkylsulfonic acid or inorganic acid having a pKa of not more than 3; and
(BH)⁺ is the monoprotonated form of a nitrogen-containing base B having a pKa between 0 and 5.0, and a boiling point less than 170° C., and
wherein B is selected from the group consisting of:

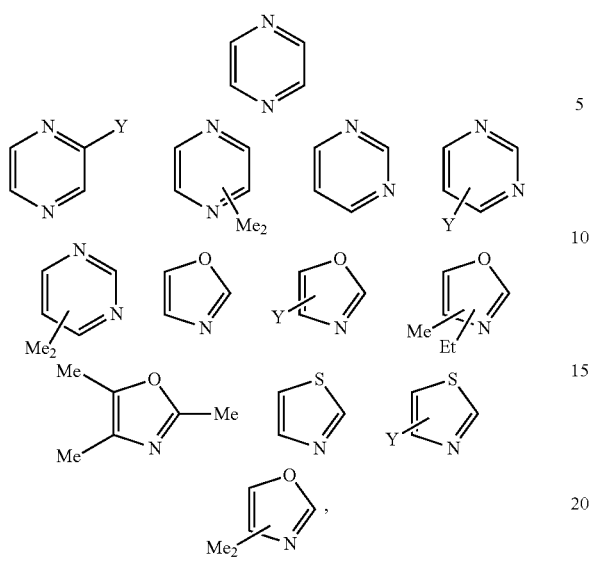
in which Y is methyl or ethyl.
16. The thermal acid generator of claim 15, wherein $A^-$ is the anion of a fluoroalkylsulfonic acid.
* * * * *